United States Patent
Sommer

(10) Patent No.: US 8,596,264 B2
(45) Date of Patent: Dec. 3, 2013

(54) INHALATION NEBULIZER

(75) Inventor: Erik Sommer, Schoneiche bei Berlin (DE)

(73) Assignee: Pari GmbH Spezialisten für effektive Inhalation, Starnberg (DE)

(*) Notice: Subject to any disclaimer, the term of this patent is extended or adjusted under 35 U.S.C. 154(b) by 2787 days.

(21) Appl. No.: 10/182,748

(22) PCT Filed: Feb. 2, 2001

(86) PCT No.: PCT/EP01/01156
§ 371 (c)(1),
(2), (4) Date: Oct. 29, 2002

(87) PCT Pub. No.: WO01/56639
PCT Pub. Date: Aug. 9, 2001

(65) Prior Publication Data
US 2003/0089366 A1    May 15, 2003

(30) Foreign Application Priority Data

Feb. 2, 2000   (DE) .................................. 100 04 465

(51) Int. Cl.
*A61M 15/00* (2006.01)
*A61M 16/00* (2006.01)

(52) U.S. Cl.
USPC ............. 128/200.21; 128/200.14; 128/203.13

(58) Field of Classification Search
USPC ............. 128/200.14–200.24, 203.12, 203.15, 128/203.13
See application file for complete search history.

(56) References Cited

U.S. PATENT DOCUMENTS

| 3,354,022 | A | * | 11/1967 | Johnson, Jr. et al. | 428/167 |
| 3,522,806 | A | * | 8/1970 | Szekely | 128/200.18 |
| 4,003,559 | A | * | 1/1977 | Kuwano et al. | 266/204 |
| 4,177,945 | A | * | 12/1979 | Schwartz et al. | 239/338 |
| 4,335,770 | A | * | 6/1982 | Kulle et al. | 604/408 |
| 4,823,784 | A | * | 4/1989 | Bordoni et al. | 128/200.14 |
| 5,611,332 | A | * | 3/1997 | Bono | 128/200.18 |
| 5,738,086 | A | * | 4/1998 | McMahon et al. | 128/200.21 |

FOREIGN PATENT DOCUMENTS

| DE | 198 07 682 | | 8/1999 | | |
| EP | 0 170 715 | | 2/1986 | | |
| EP | 0 642 992 | | 3/1995 | | |
| EP | 0 694 314 | | 1/1996 | | |
| EP | 0911047 | * | 4/1999 | | 128/200.14 |
| EP | 0 933 388 | | 8/1999 | | |
| WO | 96/04123 | * | 2/1996 | | 428/167 |
| WO | 96/32345 | | 10/1996 | | |
| WO | 99/42154 | | 8/1999 | | |
| WO | 01/56639 | | 8/2001 | | |

* cited by examiner

*Primary Examiner* — Gary Jackson
*Assistant Examiner* — Michael Mendoza
(74) *Attorney, Agent, or Firm* — Merchant & Gould P.C.

(57) ABSTRACT

The inhalation nebulizer according to the invention has a liquid reservoir, whose surface facing the liquid to be nebulized has a surface structure comprising protrusions and indentations, of which at least the protrusions consist of hydrophobic materials or permanently hydrophobized materials.

8 Claims, 1 Drawing Sheet

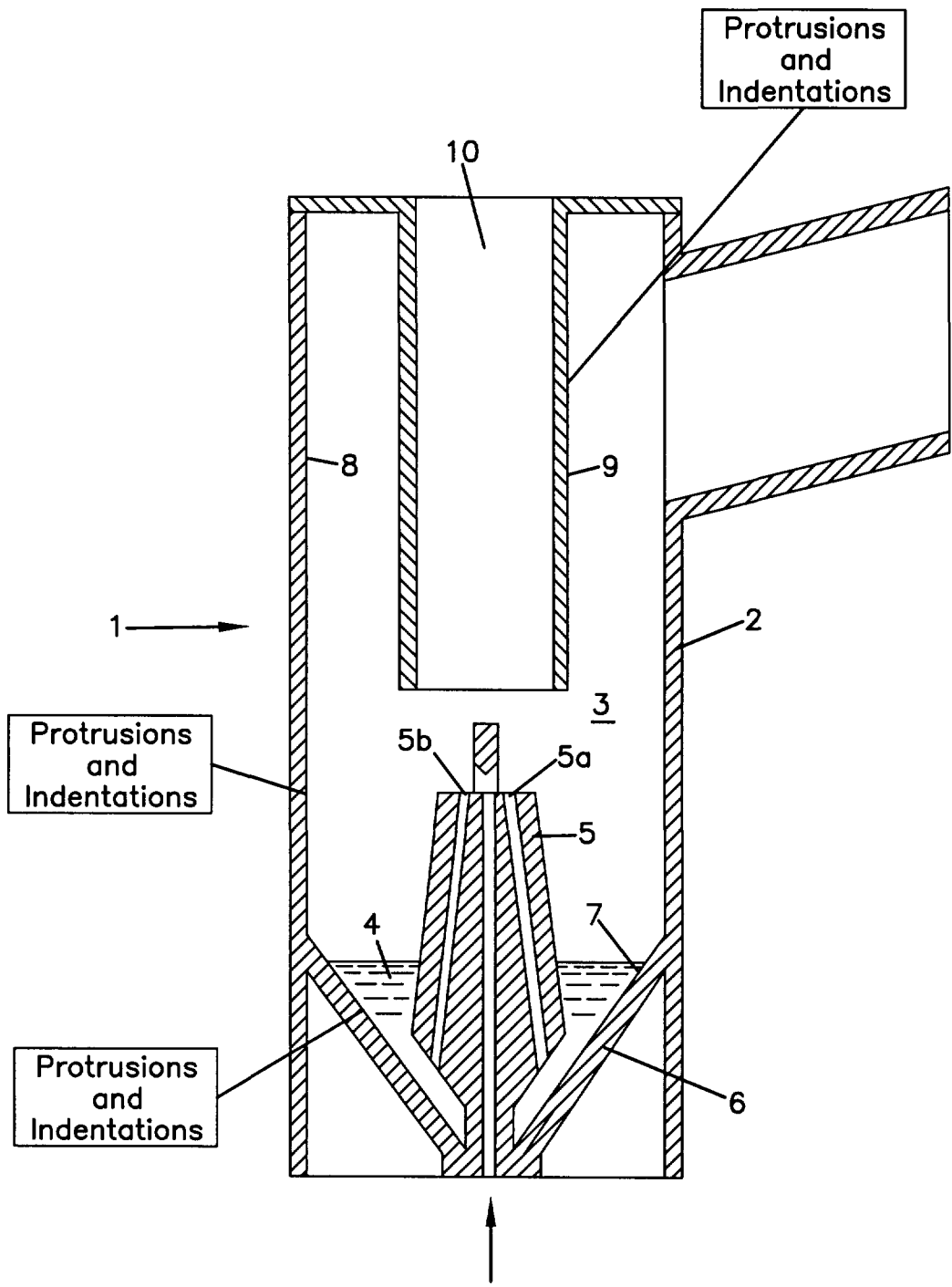

INHALATION NEBULIZER

The invention relates to inhalation nebulizers having a liquid reservoir for a liquid to be nebulized.

By means of inhalation nebulizers therapeutically effective or medicament-containing liquids are nebulized to an aerosol by means of an aerosol generator which regularly consists of respirable particles. The prepared aerosol is presented to a patient for inhalation in the course of an inhalation therapy, whereby the therapeutically effective liquid or the medicament enters the respiratory passages of the patient.

BACKGROUND OF THE INVENTION

Inhalation nebulizers of this kind are known in different embodiments. Thus, for example, EP 0 170 715 A1 discloses an inhalation nebulizer in which, among others, liquid substances are nebulized by means of a pressurized gas flow. As an aerosol generator, a nozzle is arranged in a nebulizing chamber of the inhalation nebulizer and has two suction channels arranged beside a pressurized gas channel. When pressurized air flows through the pressurized gas channel, the liquid to be sprayed is sucked through the suction channels. For this purpose, the suction channels protrude into a container in which the liquid to be sprayed is stored. An inhalation nebulizer which operates according to the same principle is known from EP 0 694 314 A1, in which however, in order to improve the dosage accuracy, a container insert is provided for the spraying substance. This design is proposed taking into account the requirement that the exact dosage of the medicament to be administered is especially important for medical applications. In the inhalation nebulizers known this requirement is met in that exactly defined amounts of the medicament are presented for spraying.

In the inhalation nebulizers of the kind described herein, the amount of liquid presented for spraying is never the same as the actually nebulized amount of liquid, so that the amount of the medicament offered to the patient for inhalation is always smaller than the amount of the medicament filled in the inhalation nebulizer. In particular for liquids containing medicaments it can be observed that the concentration of the medicament in the liquid remaining in the nebulizer increases in the course of the inhalation treatment.

SUMMARY OF THE INVENTION

Starting from this prior art, the problem underlying the present invention consists in that to further develop the known inhalation nebulizers such that a greater dosage accuracy is obtained, i.e. that the liquid nebulized by the inhalation nebulizer and the effective dose administered to the patent can be determined more exactly.

This problem is solved by an inhalation nebulizer with a liquid reservoir for a therapeutically effective or medicament-containing liquid to be nebulized, whose surface of the liquid reservoir facing the liquid has a surface structure comprising protrusions and indentations, of which at least the protrusions of the surface structure consist of hydrophobic materials or permanently hydrophobized materials and the protrusions are not removable by the liquid, by water or by water with detergents.

By the design of the inhalation nebulizer of the invention it is achieved that the liquid or the medicament contained therein will not adhere to the surface of the liquid reservoir. Thereby, loss of liquid is avoided due to wetting of the surfaces. Further, the recirculation of the liquid to the suction area of the aerosol generator is facilitated by correspondingly designed nebulizers. The dosage accuracy is increased to a substantial extent in those cases in which the medicament particles contained in the liquid adhere to a greater extent to the surface which was not designed according to the invention than does the liquid itself. By the surface structure according to the invention the object is achieved that the medicament always remains in the liquid and, thus, can be nebulized with greater reliability.

In a preferred embodiment, the distance between the protrusions of the surface structure according to the invention has a range of from 1 to 300 µm. The height of the protrusions has a range of from 1 to 100 µm.

Further, the use of a polymer as a hydrophobic material is advantageous.

In order to exclude that other areas, because of the adhering liquid or the adhering medicament, participate in an undefined decrease of the amount of liquid or medicament to be nebulized, a further embodiment provides that the surface of the inhalation nebulizer housing facing the nebulizing chamber has also the surface structure described above. In a further embodiment, this surface structure is also provided on the surfaces of an air intake chimney disposed in the nebulizing chamber. In the end, all surfaces of the inhalation nebulizer facing the nebulizing chamber may be equipped with the surface structure according to the invention, in order to optimally avoid loss of liquid or loss of medicament because of wetting and adhering. However, it should be noted that the greatest contribution to the increase of the dosage accuracy makes the design of the surface of the liquid reservoir according to the invention.

The surface structure to be provided according to the invention may be produced in different ways, as is e.g. described in EP 0 772 514 A1 for self-cleaning surfaces. Here, it is surprising that a surface which is proposed for large objects such as car bodies, building facades and the like for the prevention of pollution can also be applied in the field of inhalation nebulizers for an increase of the dosage accuracy.

BRIEF DESCRIPTION OF THE DRAWINGS

FIG. 1 is a side sectional view of an inhalation nebulizer according to the principles of the present invention.

In the following, the invention will be described in detail by means of an embodiment with reference to the accompanying FIG. 1.

DETAILED DESCRIPTION OF THE PREFERRED EMBODIMENT

The inhalation nebulizer shown in FIG. 1 consists of a housing 2 including a nebulizing chamber 3 into which the liquid 4 to be nebulized is sprayed by means of an aerosol generator 5. During use, the liquid 4 is contained in a liquid reservoir 6 which is designed such that the liquid accumulates at the bottom of the aerosol generator and may be sucked via the suction channels 5a and 5b of the aerosol generator 5.

The aerosol generator according to the present embodiment is a spray nozzle. However, the invention is not limited to inhalation nebulizers of this kind of aerosol generators.

According to the invention, the surface 7 of the liquid reservoir is equipped with a surface structure comprising protrusions and indentations. Protrusions and indentations are represented in FIG. 1 by a 'black box'. At least the protrusions of the surface structure consist of hydrophobic materials, preferably of polymers, or of permanently hydrophobized materials. The distance between the protrusions has a range of from 1 to 300 µm, preferably of from 5 to 200 µm.

The height has a range of from 1 to 100 µm. In order to obtain the effect of the invention, the protrusions cannot be removed neither by the liquid, nor by water or water with detergents.

By the surface 7 designed in accordance with the invention it is assured that no wetting will take place so that the liquid and/or the medicament will be led to an increased extent to the bottom of the nozzle and, thus, to the suction channels 5a and 5b of the aerosol generator 5.

Further, the internal surface 8 of the inhalation nebulizer 1 shown in the FIGURE, i.e. the surface which substantially encompasses the nebulizing chamber 3, has a surface structure comprising protrusions and indentations. Protrusions and indentations are represented by a 'black box'. The surface structure corresponds to the surface structure of the liquid reservoir, but must not be identical in the concrete embodiment. The distance of the protrusions may e.g. be smaller in the area of the liquid reservoir, and may be greater in the area of the nebulizing chamber.

Similarly, the surface structure according to the invention may be provided on the surface 9 of the air intake chimney 10, e.g., protrusions and indentations are represented by a 'black box'. Here, the concrete design does not need to be in concurrence with the surface 7 of the liquid reservoir 6 or the surface 8 of the nebulizer housing 2 either.

The invention claimed is:

1. An inhalation nebulizer having a liquid reservoir for a therapeutically effective or medicament-containing liquid to be nebulized, wherein a surface of the liquid reservoir facing the liquid has a surface structure comprising protrusions having a distance therebetween in the range of from 1 to 200 µm and a height in the range of from 1 to 100 µm, with at least the protrusions comprising hydrophobic materials or permanently hydrophobized materials, and wherein the protrusions are not removable by the liquid, by water or by water with detergents.

2. The inhalation nebulizer of claim 1, wherein the hydrophobic material is a polymer.

3. The inhalation nebulizer according to claim 1, comprising a nebulizing chamber in which the liquid is nebulized, and wherein a surface of the inhalation nebulizer facing the nebulizing chamber has a surface structure comprising protrusions, with at least the protrusions comprising hydrophobic materials or permanently hydrophobized materials, and wherein the protrusions are not removable by the liquid, by water or by water with detergents.

4. The inhalation nebulizer of claim 3, wherein the surface structure of the inhalation nebulizer facing the nebulizing chamber comprises protrusions and indentations.

5. The inhalation nebulizer according to claim 1, further comprising an aerosol generator in the liquid reservoir, and wherein the liquid reservoir is designed such that a recirculation of the liquid in a suction area of the aerosol generator is performed.

6. The inhalation nebulizer of claim 5, further comprising an air intake chimney in the nebulizing chamber, wherein surfaces of the air intake chimney, which are arranged in the nebulizing chamber, have a surface structure comprising protrusions, with at least the protrusions of the surface structure comprising hydrophobic materials or peiinanently hydrophobized materials, and wherein the protrusions are not removable by the liquid, by water or by water with detergents.

7. The inhalation nebulizer of claim 6, wherein the surface structure of the air intake chimney comprises protrusions and indentations.

8. The inhalation nebulizer of claim 1, wherein the surface structure of the liquid reservoir comprises protrusions and indentations.

\* \* \* \* \*